US008541383B2

(12) United States Patent
Gokaraju et al.

(10) Patent No.: US 8,541,383 B2
(45) Date of Patent: Sep. 24, 2013

(54) SYNERGISTIC PHYTOCHEMICAL COMPOSITION FOR THE TREATMENT OF OBESITY

(75) Inventors: Ganga Raju Gokaraju, Vijayawada (IN); Rama Raju Gokaraju, Vijayawada (IN); Trimurtulu Golakoti, Vijayawada (IN); Venkateswara Rao Chirravuri, Vijayawada (IN); Venkateswarlu Somepalli, Vijayawada (IN); Kiran Bhupathiraju, Vijayawada (IN)

(73) Assignee: Laila Nutraceurticals, Vijayawada (IN)

( * ) Notice: Subject to any disclaimer, the term of this patent is extended or adjusted under 35 U.S.C. 154(b) by 0 days.

(21) Appl. No.: 12/784,295

(22) Filed: May 20, 2010

(65) Prior Publication Data

US 2010/0227828 A1    Sep. 9, 2010

Related U.S. Application Data

(63) Continuation of application No. PCT/IN2007/000544, filed on Nov. 22, 2007.

(51) Int. Cl.
| | | |
|---|---|---|
| *A61K 31/70* | (2006.01) | |
| *A61K 31/12* | (2006.01) | |
| *A61K 36/00* | (2006.01) | |
| *A01N 43/04* | (2006.01) | |
| *A01N 35/00* | (2006.01) | |
| *A01N 65/00* | (2009.01) | |

(52) U.S. Cl.
USPC ............... 514/27; 514/25; 514/679; 424/725

(58) Field of Classification Search
USPC ............................. 514/27, 25, 679; 424/725
See application file for complete search history.

(56) References Cited

U.S. PATENT DOCUMENTS

| | | | |
|---|---|---|---|
| 5,266,344 A | 11/1993 | Mimura et al. | |
| 5,494,668 A | 2/1996 | Patwardhan | |
| 6,080,401 A | 6/2000 | Reddy et al. | |
| 6,264,995 B1 | 7/2001 | Newmark et al. | |
| 6,413,553 B1 | 7/2002 | Bandyopadhyay et al. | |
| 6,440,468 B1 | 8/2002 | Quintanilla Almagro et al. | |
| 6,500,470 B1 | 12/2002 | Pauly | |
| 6,521,271 B1 | 2/2003 | Phan | |
| 6,667,047 B2 | 12/2003 | Brown et al. | |
| 6,746,694 B1 | 6/2004 | Bhadra et al. | |
| 6,773,728 B2 | 8/2004 | Bandyopadhyay et al. | |
| 6,780,441 B2 | 8/2004 | Solanki | |
| 6,900,356 B2 | 5/2005 | Gokaraju et al. | |
| 6,979,470 B2 | 12/2005 | Babish et al. | |
| 6,989,165 B2 * | 1/2006 | Pushpangadan et al. | ..... 424/754 |
| 7,070,817 B2 | 7/2006 | Kuppam | |
| 2002/0086068 A1 | 7/2002 | Bandyopadhyay et al. | |
| 2003/0096027 A1 | 5/2003 | Babish et al. | |
| 2003/0108628 A1 | 6/2003 | Babish et al. | |
| 2003/0113391 A1 | 6/2003 | Brown et al. | |
| 2003/0152585 A1 | 8/2003 | Solanki | |
| 2003/0216600 A1 | 11/2003 | Gokaraju et al. | |
| 2004/0001896 A1 | 1/2004 | Kuppam | |
| 2004/0009240 A1 | 1/2004 | Solanki | |
| 2004/0247700 A1 | 12/2004 | Babish et al. | |
| 2005/0129791 A1 | 6/2005 | Babish et al. | |
| 2005/0191375 A1 | 9/2005 | Babish et al. | |
| 2005/0267221 A1 * | 12/2005 | Wellen | .......................... 514/688 |
| 2006/0147439 A1 * | 7/2006 | Upadhyay et al. | ........... 424/94.2 |
| 2006/0165826 A1 | 7/2006 | Rao et al. | |
| 2006/0222682 A1 | 10/2006 | Andrews | |
| 2006/0275247 A1 | 12/2006 | Helman et al. | |
| 2007/0042055 A1 | 2/2007 | Palpu et al. | |
| 2007/0072931 A1 | 3/2007 | Sinha et al. | |

FOREIGN PATENT DOCUMENTS

| | | |
|---|---|---|
| AU | 2000075253 A5 | 6/2001 |
| AU | 2348721 A | 8/2004 |
| AU | 2001235968 B2 | 3/2005 |
| CN | 1652805 A | 8/2005 |
| CN | 1735355 A | 2/2006 |
| EP | 1064008 B1 | 1/2001 |
| EP | 1133992 A1 | 9/2001 |
| EP | 1414475 A1 | 5/2004 |
| EP | 1571929 A1 | 9/2005 |
| EP | 1331939 A | 9/2006 |
| FR | 2655054 A1 | 5/1991 |
| GB | 2388539 A1 | 11/2003 |
| GB | 2426453 A1 | 11/2006 |
| JP | 07304685 A2 | 11/1995 |
| JP | 2002121144 A2 | 4/2002 |
| WO | 9703674 A1 | 6/1997 |
| WO | 9948512 A1 | 9/1999 |
| WO | 0232440 A1 | 4/2002 |

(Continued)

OTHER PUBLICATIONS

Gove et al., Webster's Third New International Dictionary, 1963, p. 1798.*
"Obesity", Merck Manual Online Edition, [retrieved on May 11, 2011]. Retrieved from the Internet <http://www.merckmanuals.com/home>. Revision Aug. 2008, 9pp.*
http://www.cdc.gov/nchs/products/pubs/pubd/hestats/overweight/overwght_adult_03.html (Updated Jun. 2010, now found at http://www.cdc.gov/nchs/data/hestat/obesity_adult_07_08/obesity_adult_07_08.htm) viewed May 10, 2012.
WHO's fact sheet No. 311, Sep. 2006, http://www.who.int/mediacentre/factsheets/fs311/en/index.html (updated Mar. 2011, now found at http://www.who.int/mediacentre/factsheets/fs311/en/), viewed May 10, 2012.

(Continued)

*Primary Examiner* — Eric S. Olson
*Assistant Examiner* — Zhengfu Wang
(74) *Attorney, Agent, or Firm* — Kramer Amado, P.C.

(57) ABSTRACT

Synergistic anti-adipogenic and pro-lipolytic compositions for the prevention and amelioration of adipogenesis and lipolysis mediated diseases, comprising at least two extracts selected from enriched demethylated curcuminoids obtained from *Curcuma longa*, *Moringa oleifera* and *Murraya koenigii*. The anti-adipogenic and pro-lipolytic compositions optionally contain one or more anti-obesic agents. These compositions are useful for preventing anti-inflammatory and free radical mediated diseases.

30 Claims, 3 Drawing Sheets

(56) References Cited

FOREIGN PATENT DOCUMENTS

| WO | 0249655 A1 | 6/2002 |
| --- | --- | --- |
| WO | 03006036 A2 | 1/2003 |
| WO | 03013564 A2 | 2/2003 |
| WO | 2004054391 A1 | 7/2004 |
| WO | 2004002507 A1 | 8/2004 |
| WO | 2005070442 A1 | 8/2005 |
| WO | 2006062681 A1 | 6/2006 |
| WO | 2006111833 A1 | 10/2006 |
| WO | 2007026203 A1 | 3/2007 |
| WO | 2007/043058 A1 | 4/2007 |

OTHER PUBLICATIONS http://ec.europa.eu/health/ph_determinants/iife_style/nutrition/green_papernutritiongp_col 83_en.pdf (now found at http://www.emhf.org/resource_images/obesity.pdf), viewed May 10, 2012.

Ziuozenkova et al., Lipolysis of triglyceride-rich lipoproteins generates PPAR ligands: Evidence for an antiinflammatory role for lipoprotein lipase. PNAS, Mar. 4, 2003, vol. 100, No. 5, 2730-2735.

H. G. Preuss, et al, Efficacy of a novel, natural extract of (—)-hydroxycitric acid (HCA-SX) and a combination of HCA-SX, niacinbound chromium and Gymnema sylvestre extract in weight management in human volunteers: A pilot study. Nutrition Research, 2004, 24, 45-48.

C. A. Haller and N. L. Benowitz. Adverse cardiovascular and central nervous system events associated with dietary supplements containing ephedra alkaloids. New England J. Medicine, 2000, 343, 1833-1838.

Mazumder et al., Curcumin Analogs with Altered Potencies against HIV-1 Integrase as Probes for Biochemical Mechanisms of Drug Action, J. Med. Chem. 1997, 40, 3057-3063.

Ammon et al., Mechanism of antiinflammatory actions of curcumine and boswellic acids, Journal of Ethnopharmacology, vol. 38, Issues 2-3, Mar. 1993, pp. 113-119.

Saura et al., Effect of ascorbic acid and curcumin on quercetin-induced nuclear DNA damage, lipid peroxidation and protein degradationm, Cancer Letters, vol. 63, Issue 3, Apr. 30, 1992, pp. 237-241 (Abstract).

Sastri, The Wealth of India, CSIR, New Delhi, India 1962, 425-429.

Jahn, S. A. Using Moringa seeds as coagulants in developing countries. J. Am. Water Works Association, 1988. vol. 80, No. 6, p. 43-50 (Abstract) (http://apps.awwa.org/waterlibrary/scholarabstract.aspx?an=JAW_0023796) viewed Jun. 19, 2012.

Nadkarni et al., The Indian Materia Medica Popular Prakasan Bombay, p. 810, 1976.

Chopra et al., Glossary of Indian Medicinal Plants, CSIR, New Delhi, p. 170, 1956.

Siddhuraju et al., Antioxidant Properties of Various Solvent Extracts of Total Phenolic Constituents from Three Different Agroclimatic Origins of Drumstick Tree (*Moringa oleifera* Lam.) Leaves, J. Agric. Food Chem. 2003, 51, 2144-2155.

Pramanik et al., Chemical investigation of aqueous extract of the mature and premature flowers of *Moringa oleifera* and Structural studies of a polysaccharide isolated from its premature flowers, Indian J Chem, 1998, 37B 676-682.

Vlahov et al., 13C NMR Characterization of Triacylglycerols of *Moringa oleifera* Seed Oil: An "Oleic-Vaccenic Acid" Oil, J. Agric. Food Chem. 2002, 50, 970-975.

Gassenschmidt, U., et. al, Isolation and characterization of a flocculating protein from *Moringa oleifera* Lam, Biochim Biophys Acta. Apr. 13, 1995;1243(3):477-81.

Faizi et al., Novel hypotensive agents, niazimin A, niazimin B, from *Moringa oleifera*: Isolation of first naturally occurring carbamates, J. Chem. Soc. Perkin Trans. 1, 1994, 3035-40.

Faizi et al., Fully acetylated carbamate and hypotensive thiocarbamate glycosides from *Moringa oleifera*, Phytochemistry, vol. 38, Issue 4, Mar. 1995, pp. 957-963.

Geuyrard et al., First synthesis of an O-glycosylated glucosinolate isolated from *Moringa oleifera*, Tetrahedron Letters, vol. 41, Issue 43, Oct. 21, 2000, pp. 8307-8309.

Sastri et al. The Wealth of India, CSIR, New Delhi, 1962, vol. 6, pp. 448-450.

Adebajo, Anti-trichomonal, biochemical and toxicological activities of methanolic extract and some carbazole alkaloids isolated from the leaves of *Murraya koenigii* growing in Nigeria, Phytomedicine, vol. 13, Issue 4, Mar. 13, 2006, pp. 246-254.

Macleod et al., Analysis of the volatile essential oils of *Murraya koenigii* and *Pandanus latifolius*, Phytochemistry, vol. 21, Issue 7, 1982, pp. 1653-1657.

Mallavarapu et al., Composition of Indian Curry Leaf Oil, Journal of Essential Oil Research vol. 11, Issue 2, 1999 (Abstract) (viewed Jun. 19, 2012).

Chakrabarty et al., Carbazole Alkaloids from *Murray koenigii*, Phytochemistry vol. 46 No. 4. pp. 751-755, 1997.

Joshi et al., On the structures of girinimbine, mahanimbine, isomahanimbine, koenimbidine and murrayacine. Tetrahedron, vol. 26, Issue 5, 1970 pp. 1475-1482.

Yadav et al., Hypoglycemic and antihyperglycemic activity of *Murraya koenigii* leaves in diabetic rats, Journal of Ethnopharmacology, vol. 82, Issues 2-3, Oct. 2002, pp. 111-116.

Nambiar et al., Drumstick Leaves as a Source of Vitamin A in ICDS-SFP. Indian J Pediatr 2003; 70(5): 383-387.

Ramsewak et al., Biologically Active Carbazole Alkaloids from *Murraya koenigii*, J. Agric. Food Chem. 1999, 47, 444-447.

Tachibana et al., Comparison of Antioxidative Properties of Carbazole Alkaloids from *Murraya koenigii* Leaves, J. Agric. Food Chem. 2003, 51, 6461-6467.

Jiang et al., Use of liquid chromatography—electrospray ionization tandem mass spectrometry to identify diarylheptanoids in turmeric (*Curcuma longa* L.) rhizome. Journal of Chromatography A, vol. 1111, Issue 1, Apr. 7, 2006, pp. 21-31.

Nakayama et al., Two curcuminoid pigments from *Curcuma domestica*. Phytochemistry, vol. 33, Issue 2, May 13, 1993, pp. 501-502.

Iqbal, Chemistry of Indigenous Medicinal Plant, *Moringa Oleifera*, Hamdard Medicus, vol. XXXI, No. 3, Jul.-Sep. 1988, pp. 88-96.

* cited by examiner

A: Protective efficacy

B: Therapeutic efficacy

US 8,541,383 B2

SYNERGISTIC PHYTOCHEMICAL COMPOSITION FOR THE TREATMENT OF OBESITY

CROSS REFERENCE TO RELATED APPLICATIONS

This application is a continuation-in-part of International Patent Application PCT/IN2007/000544 entitled "New Synergistic Phytochemical Compositions for the Treatment of Obesity," filed on Nov. 22, 2007 and published as WO 2009/066303 on May 28, 2009.

FIELD OF INVENTION

This invention relates generally to the new phytochemical compositions for reducing or preventing mammalian obesity. In particular, the invention relates to novel, synergistic compositions comprising enriched demethylated curcuminoids, extract of *Moringa oleifera*, extract of *Murraya koenigii* and biologically acceptable carrier or diluents for reducing or preventing adipose tissue mass, inflammation and free radical mediated disorders.

BACKGROUND OF THE INVENTION

Obesity is excess body weight for a particular age, sex and height as a consequence of imbalance between energy intake and energy expenditure. The primary cause of obesity is either due to overeating, inadequate exercise or eating disorder, some genetic disorders, underlying illness (e.g., hypothyroidism), certain medications, sedentary lifestyle, a high glycemic diet (i.e., a diet that consists of meals that give high post-prandial blood sugar) weight cycling (caused by repeated attempts to lose weight by dieting, eating disorders), stress and insufficient sleep.

During the past 20 years, obesity among adults has risen significantly in the United States. The latest data from the National Center for Health Statistics show that 30 percent of U.S. adults of 20 years of age and older, i.e. over 60 million people, are obese. The percentage of young people who are overweight has more than tripled since 1980. More than 16% of the children and teens aged 6-19 years, that is over 9 million young people, are considered overweight. Although, the US national health objectives for the year 2010 is to reduce the prevalence of obesity among adults to less than 15%, current data indicate that the situation is worsening rather than improving. Obesity in Europe was recognized as a serious problem, with up to 27% of men, 38% of women and 3 million children are clinically obese. The obesity was not limited to developed countries, but it was rapidly becoming a problem in developing countries as well.

As per World Health Organization's (WHO) latest projections, approximately 1.6 billion adults (age 15+) were overweight and at least 400 million adults were obese globally in 2005. WHO further projects that by 2015, approximately 2.3 billion adults will be overweight and more than 700 million will be obese.

Recent studies have shown that approximately a third of variance in adult body weights result from genetic influences. Leptin, an adipocyte and placenta-derived circulating protein, regulates the magnitude of fat stores in the body leading to obesity. Gastrointestinal peptides, neurotransmitters and adipose tissue may also have an etiologic role in obesity. Obesity and adipose tissue expansion increase the risk of hypertension, type 2 diabetes, arthritis, elevated cholesterol, cancer and serious hormonal imbalances in women, leading to sterility. Obesity also increases the risk of, dyslipidemia (for example, high total cholesterol or high levels of triglycerides), gallbladder disease, osteoarthritis, sleep disorders, respiratory problems, arteriosclerosis and heart failure.

Obesity is the culmination of many underlying mechanisms. Obesity is characterized as uncontrolled adipose tissue mass in the body and recognized as the fastest growing metabolic disorder in the world. An increase in adipose tissue mass can be the result of the production of new fat cells through the process of adipogenesis and/or the deposition of increased amounts of cytoplasmic triglyceride or lipid droplets per cell. In the adipogenesis process, proliferation of preadipocytes or precursor fat cells needs to be followed by the differentiation of these cells to the mature adipocyte phenotype. Increased lipid accumulation in the mature adipocyte cells is the most important feature of obesity disorder. Peroxisome Proliferator-Activator Receptor gamma (PPAR-$\gamma$) is predominantly expressed in adipocytes and is a key determination factor for adipogenesis.

Fat is stored as triglycerides form in adipose tissue. The breakdown of this fat in fat cells into glycerol and fatty acids is known as lipolysis. The body's adrenergic system plays a major part in regulating energy expenditure and lipolysis. In this process catecholamines mobilize energy-rich lipids by stimulating lipolysis in fat cells and thermogenesis in brown adipose tissue and skeletal muscle. It is known that PPAR alpha plays an important role in regulating lipolysis through the control of lipid metabolic enzymes such as lipoprotein lipase (LPL).

Effective anti-obese therapies with satisfactory efficacy and acceptable safety have been long overdue. More importantly, anti-obese agents of natural origin with proven safety are greatly needed to control the growing menace. Many herbal and natural products containing gymnema extract, garcinia extract, or carnitine, for example are known to prevent fat accumulation through the inhibition of fat absorption, enhancement of fat decomposition, and the enhancement of fat consumption by the body. It is particularly advantageous for inhibition, amelioration and prevention of obesity if an anti-obesity action can be imparted to food products and beverages, which are ordinarily ingested.

It is therefore an object of the present invention to provide a non-toxic dietary supplement composition comprising enriched demethylated curcuminoids from *Curcuma longa* alone or at least two of the compounds or extracts selected from enriched demethylated curcuminoids, *Moringa oleifera* and *Murraya koenigii* and optionally containing other ingredients.

A yellow pigmented fraction isolated from the rhizomes of *Curcuma longa* contains curcuminoids belonging to the dicinnamoyl methane group. They are considered the most important active ingredients and are believed to be responsible for the biological activity of *Curcuma longa*. Though their major activity is anti-inflammatory, curcuminoids have been reported to possess antioxidant, antiallergic, wound healing, antispasmodic, antibacterial, antifungal, antitumor and anti-HIV activity as well. The major curcuminoids isolated from *Curcuma longa* include curcumin, demethoxycurcumin and bisdemethoxycurcumin. Curcuminoids may be found in other botanicals in addition to *Curcuma longa*, such as *Curcuma xanthorrhiza* and *Curcuma zedoaria*. Curcuminoids are well known for their anti-inflammatory activity. Turmeric is one of the oldest anti-inflammatory drugs used in Ayurvedic medicine. Demethylated curcumin, a minor curcuminoid from *Curcuma longa* is highly potent compared to the curcuminoids. The pharmacokinetics involving the safety, toxicity, dose range and biological properties of turmeric and its components, including curcumin is known.

The anti-inflammatory properties of curcumin were shown to inhibit the 5-lipoxygenase activity in rat peritoneal neutrophils as well as the 12-lipoxygenase and the cyclooxygenase activities in human platelets. Curcumin had no significant effect on quercetin-induced nuclear DNA damage, lipid peroxidation and protein degradation and thus has the unique potential of acting as both pro- and antioxidants, depending on the redox state of their biological environment.

The Moringaceae is a single genus family with 14 known species. Of these, *Moringa oleifera* Lam. (syns: *Moringa pterygosperma* Gaertn.) is the most widely known and utilized species. The tree ranges in height from 5-12 m with an open, umbrella shaped crown, straight trunk (10-30 cm thick) with corky, whitish bark. A native of the sub-Himalayan regions of North West India, *Moringa oleifera* (*M. oleifera*) is now indigenous to many countries in Africa, Arabia, South East Asia, the Pacific and Caribbean Islands and South America. It is now being cultivated in the tropical and subtropical areas around the worldwide. *M. oleifera* commonly known as the 'horse-radish' tree (arising from the taste of a condiment prepared from the roots) and 'drumstick' tree (arising from the shape of the pods) and with many other vernacular names, indicating its significance around the world.

The leaves, pods, seeds, flowers, and roots of the *Moringa oleifera* tree are edible. The leaves have been proved by scientific research to be a powerhouse of nutritional value. It contains 7 times the vitamin C in oranges, 4 times the calcium in milk, 4 times the vitamin A in carrots and 2 times the protein in milk. Even though the tender pods, commonly known as 'Drumstick' are considered a prized vegetable for culinary preparations, the tender leaves are also used for curry preparation.

*Moringa* is one of the most useful plant used as food and in indigenous system of medicine. It also has medicinal importance in folk medicine for treatment of variety of human ailments like rheumatism, paralysis, epilepsy.

Photochemical investigations of different parts of *M. oleifera* on its resulted in the isolation and characterization of various chemical constituents such as flavonoids, carbohydrates, essential oils & lipids, amino acids & vitamins, proteins and glucosinolates and glucosinolates—derived hydrolysis products such as isothiocyanates, nitriles and carbamates.

*Murraya koenigii*, more commonly known as curry leaf, is a small tree growing up to 4-6 m tall, with a trunk up to 40 cm diameter. The flowers are small white, and fragrant. The small black, shiny berries are claimed to be edible, but their seeds are poisonous. The curry tree is native to India; today found almost everywhere in the Indian subcontinent excluding the high altitudes of the Himalayas.

Curry leaf is an essential leafy spice used in Asian cuisines for its distinct flavor. It has prominently been used a folk medicine in India and other Asian countries as an analgesic, astringent, antidysenteric, febrifuge, hypolipidemic and hypoglycemic agent. It is a powerful antioxidant and used for improvement of vision. It has also been used to treat nightblindness, and for regulation of fertility. The green leaves are stated to be eaten raw for curing dysentery, and the infusion of the washed leaves stops vomiting. The leaves, the bark and the roots of *Murraya koenigii* can be used as a tonic for stomachic. The green leaves are stated to be eaten raw for curing dysentery, and the infusion of the washed leaves stops vomiting. A toxicity study showed that methanolic extract was moderately toxic ($LD_{50}$=316.23 mg/kg body weight) to rats.

However *Murraya koenigii* has a history of hundreds of years of culinary usage by many cultures in the Eastern part of the globe.

The volatile low molecular compounds such as: $\beta$-caryophyllene, $\beta$-gurjunene, $\beta$-elemene, $\beta$-phellandrene, $\beta$-thujene, $\alpha$-selinene, $\beta$-bisabolene, limonene, $\beta$-trans-ocimene and $\beta$-cadinene in the essential oil are mostly responsible for the characteristic aroma of curry leaves. Carbazole alkaloids, 9-carbethoxy-3-methylcarbazole 9-formyl-3-methylcarbazole and 3-methyl-carbazole and another alkaloid murrayacinine were isolated from the roots of *Murraya koenigii*. A quality study indicated that the fresh curry leaves obtained from the three New England states contained 9744 ng of lutein, 212 ng of alpha-tocopherol, and 183 ng of beta-carotene per gram fresh weight.

Administration of curry leaves to alloxan and STZ induced diabetic rats showed hypoglycemic and anti-hyperglycemic effect. The murraya carbazole alkaloids named murrayanine and 8,8'-biskoenigii ne showed antiosteoporotic activity. The carbazole alkaloids also showed mosquitocidal and antimicrobial activities and exhibited topoisomerase I and II inhibition activities. Curry leaf reduces blood cholesterol and glucose levels in ob/ob mice. The leaves showed potent antioxidant activity both in vitro and in vivo.

The inventors of the present invention have discovered in an unexpected and surprising manner that the enriched demethylated curcuminoids, *Murraya koenigii* plant extract and *Moringa oleifera* plant extract have a novel property, which is beneficial for weight management.

The inventors further established the fact that the compositions comprising enriched demethylated curcuminoids, an extract of *Moringa oleifera* and an extract of *Murraya koenigii* have synergism, which means the compositions or mixtures have stronger effect than the sum of the individual components.

OBJECTS OF THE PRESENT INVENTION

The main object of the present invention is to develop a synergistic phytochemical composition useful for the treatment of obesity, total cholesterol level, phospholipids and triglycerides.

Yet another object of the present invention is to develop a composition useful in treating obesity, atherosclerosis and thereby to help keep slim.

Another object of the present invention is to provide synergistic compositions comprising at least two of the extracts or compounds selected from enriched demethylated curcuminoids, *Moringa oleifera* plant extract, and *Murraya koenigii* plant extract for preventing and/or reducing adipose tissue mass in obese people and also for preventing inflammatory diseases.

Still another object of the present invention is the use of enriched demethylated curcuminoids for preventing and/or reducing adipose tissue mass in obese people and also for reducing total serum cholesterol level, phospholipids and triglycerides.

Still another object of the present invention is the compositions derived from *Moringa oleifera* plant extract for treatment of hyperlipidemia/obesity, total serum cholesterol by preventing or reducing adipose tissue mass.

Still another object of the present invention is the use of *Murraya koenigii* plant extract for preventing and/or reducing adipose tissue mass by inhibiting adipogensis activity.

SUMMARY OF THE PRESENT INVENTION

In accordance with the above objectives, the invention provides compositions comprising at least two of the extracts or compounds selected from enriched demethylated curcuminoids, *Moringa oleifera* plant extract, *Murraya koenigii* plant extract and pharmaceutical carriers, useful in regulating body weight by inhibiting adipogenesis activity when administered to an obese animal, including human.

One aspect of the invention provides enriched demethylated curcuminoids from *Curcuma longa* and its dietary/pharmaceutical preparations, which potentially inhibit adipogenesis activity and accelerate lipolysis activity and is useful for the treatment of obesity.

In another aspect, the invention provides the plant extract of *Moringa oleifera* containing phyto constituents, Kaempferol-3-O-glucoside of formula V, Quercitin-3-O-glucoside of formula VI, Niazinin A of formula VII, Niazinin B of formula VIII, which inhibits adipogenesis activity and produces therapeutic benefit in regulating body weight.

Accordingly, the invention provides dietary/pharmaceutical preparations comprising the *Moringa oleifera* extract.

In a further aspect, the invention provides the *Murraya koenigii* plant extract and its dietary/pharmaceutical preparations inhibits adipose tissue mass and produces a therapeutic benefit in regulating body weight.

In another aspect, the invention provides dietary/pharmaceutical supplemental composition comprises enriched demethylated curcuminoids in the range between 1-25% by wt., *Moringa oleifera* plant extract in the range between 40-70% and *Murraya koenigii* plant extract in the range between 25-45% shows synergistic anti-adipogensis activity and is useful for controlling body weight or obesity.

In another aspect, the invention provides the dietary/pharmaceutical supplemental composition comprises enriched demethylated curcuminoids in the range between 1-25% by wt., *Moringa oleifera* plant extract in the range between 40-70% and *Murraya koenigii* plant extract in the range between 25-45%, exhibits 5-lipoxygenase inhibitory activity and is useful for preventing and/or reducing 5-lipoxygenase mediated disorders.

It has also been experimentally proved that the dietary/pharmaceutical supplemental composition comprises enriched demethylated curcuminoids in the range between 1-15% by wt., *Moringa oleifera* plant extract in the range between 40-70% and *Murraya koenigii* plant extract in the range between 25-45% shows good antioxidant activity and is useful for preventing and/or reducing free radical mediated diseases.

DETAILED DESCRIPTION OF THE PRESENT INVENTION

The invention will now be described in detail in connection with certain preferred and optional embodiments, so that various aspects thereof may be more fully understood and appreciated, it is not intended to limit the invention to these particular embodiments.

In the adipogenesis process, proliferation of preadipocytes needs to be followed by the differentiation of these cells to the mature adipocyte phenotype. Increased lipid accumulation in the mature adipocyte cells is the most important feature of this maturation process.

The uncontrolled fat accumulation in the body during the metabolic process is predominantly driven by the following key events. 1). Over expression and increased activity of Protein Tyrosine Phosphatase 1B during the differentiation process of preadipocytes to mature adipocytes, 2). Highly increased lipid accumulation was noted in the differentiated mature adipocytes, 3). Over expression and increased activity of Peroxisome Proliferator-Activated Receptor-gamma (PPAR-γ) a ligand activated nuclear receptor that acts as a lipid sensor, integrating the homeostatic control of energy, lipid, and glucose metabolism.

Thermogenesis is a metabolic process in which calories consumed and stored as fat by the body are expended to dissipate energy as a heat. This metabolic process primarily occurs in adipocytes, such as brown adipose tissue. Stimulation of thermogenesis causes fat cells to burn enemy and a consequence of this can be loss of body weight.

More importantly, anti-obese agents of natural origin with proven safety are greatly needed to control the growing menace. It is particularly advantageous for inhibition, amelioration and prevention of obesity if an anti-obesity action can be imparted to food products and beverages, which are ordinarily ingested.

Based on the above information, inventors of the present invention have undertaken screening strategy of many plant extracts using in vitro cell based experimental protocols followed by in vivo experimental studies and found that demethylated curcuminoid and extracts or fractions of *Moringa oleifera* and *Murraya koenigii* exhibit potent anti-adipogenic action by inhibiting lipid accumulation in vitro. The enriched demethylated curcuminoid extract and extract of *Murraya koenigii* also exhibit potent pro-lipolytic activity. A composition containing these three exhibited synergistic anti-adipogenic activity, which is the subject matter of the present invention.

Accordingly, synergistic anti-adipogenic and pro-lipolytic compositions for the prevention and amelioration of adipogenesis and lipolysis mediated diseases, comprising at least two extracts selected from enriched demethylated curcuminoids obtained from *Curcuma longa*, methanol extract of *Moringa oleifera* and 60% methanol extract of *Murray koenigii* along with one or more biologically acceptable carriers and optionally containing one or more of known anti-obesic agents.

Figure 1:
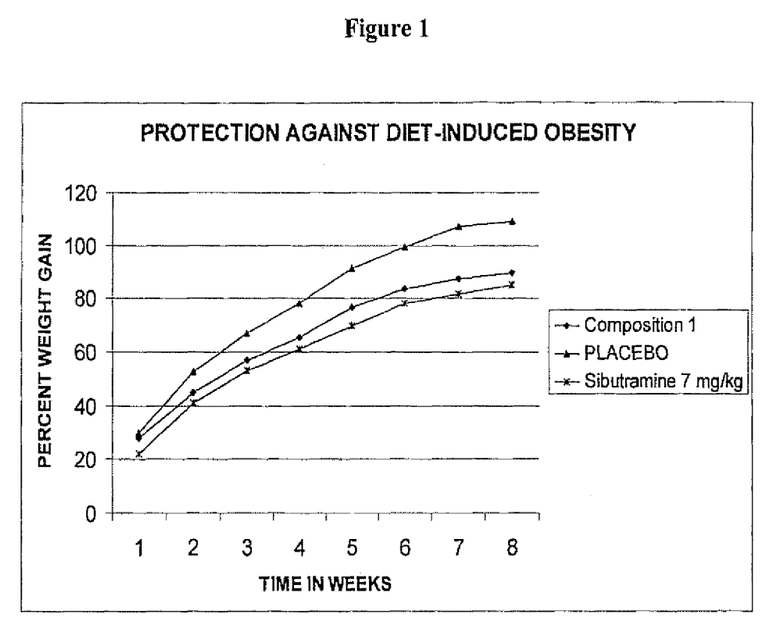
FIG. 1 represents protective anti-obese activity of composition-1 (A combination of unit doses of demethylated curcuminoids 95% and methanol extracts of *Moringa oleifera* leaf and 60% methanol extract of *Murraya koenigii* leaf in the ratio of 1:12:7) (250 mg/kg body weight) against diet induced obesity.
Figure 2:
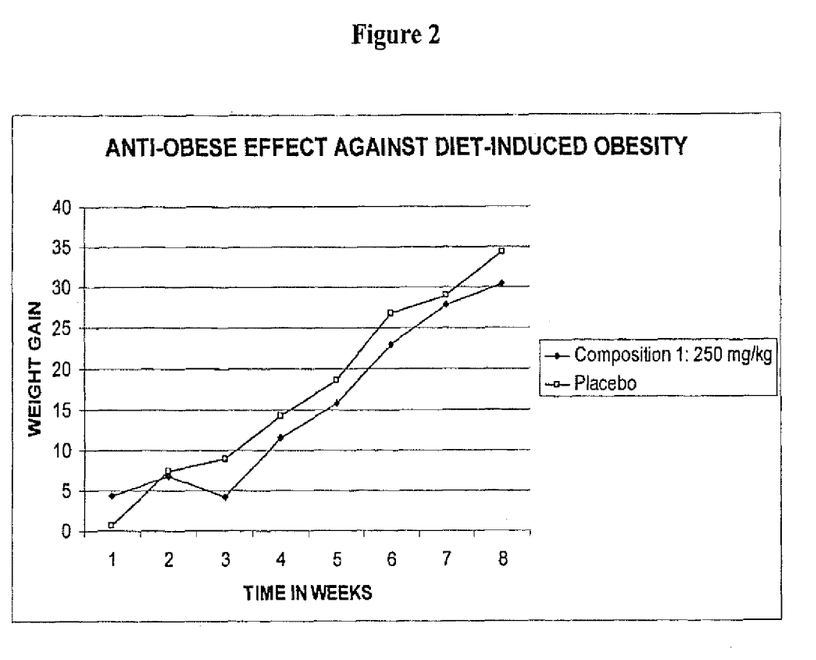
FIG. 2 represents therapeutic antiobese efficacy of composition-1 (250 mg/kg body weight) against diet induced obesity.

A composition of demethylated curcuminoids 95%, methanol extract of *Moringa oleifera* and 60% methanol extract of *Murraya koenigii* was tested for their protective efficacy and therapeutic efficacy against diet induced obesity in Sprague-Dawley rats (FIGS. 1 and 2). This composition conferred significant protection from weight gain in diet induced obese animals (FIG. 1). It has also shown therapeutic efficacy against diet induced obesity (FIG. 2).

Adipose tissue is the primary source of circulating leptin and as the adipose tissue mass increases more leptin is produced in obese people. In controlled condition, it was proved that higher levels of adiposity were associated with high concentration of serum leptin. Thus the circulating leptin appears to be one of the best biological markers of obesity and that hyper lepinemia is closely associated with several metabolic disorders.

Therefore, the inventors further investigated the serum leptin levels in the treatment group. The reduction in serum leptin levels observed in the treatment group of animals supplemented with anti-adipogenic products of the present invention compared to that of controlled group may be taken as a measure of reduction in the visceral fat tissue mass and an additional indicator for the efficacy of therapeutic agent. The animals supplemented with a composition of demethylated curcuminoids 95%, extracts of *Moringa oleifera* and *Murraya koenigii* showed significant reduction in serum leptin concentration (FIG. 3) confirming its anti-adipogenic effect in animals.

The invention further relates to the use of enriched demethylated curcuminoids from *Curcuma longa* and its dietary/pharmaceutical preparations administered to an obese animal, including human, produces a therapeutic benefit in regulating body weight.

In our co-pending application PCT/IN05/00337 dated on 13/10/2005, a process for enriching demethylated curcuminoids up to 100% was disclosed. The components present in the enriched demethylated curcuminoids are shown below.

Chemical structures of the components in enriched demethylated curcuminoids

The components present in the enriched demethylated curcuminoids are all natural products. The compounds of formula I, III and IV are present in *Curcuma longa* as minor natural products (Mimura, A. et al., U.S. Pat. No. 5,266,344 and Jiang, H. et al., *J. Chromatography A*, 2006, 1111, 21-31). The compound of formula II is isolated from *Curcuma domestica* (Nakayama, R. et al., *Phytochemistry*, 1993, 33, 501-502).

Further, the scientists at National Cancer Institute screened curcuminoids and demethylated curcuminoids for anti-HIV activity. They found that the demethylated curcuminoid (formula I) inhibited HIV-1 integrase with $IC_{50}$ value below 10 µM (Mazumder, A., et. al., *J. Med. Chem.* 1997, 40, 3057).

The inventors of the present invention disclosed the use of enriched demethylated curcuminoids from *Curcuma longa* extract having 15-100% of total demethylated curcuminoids (formula I-IV) for the treatment of obesity.

The enriched demethylated curcuminoids from *Curcuma longa* extract having 15-100% of total demethylated curcuminoids (formula I-IV), particularly 95% of total demethylated curcuminoids exhibited good anti-adipogenesis activity (see table 1).

The enriched demethylated curcuminoids from *Curcuma longa* extract having 15-100% of total demethylated curcuminoids (formula I-IV), particularly 95% of total demethylated curcuminoids also reduces total serum cholesterol level, phospholipids and triglycerides.

We have disclosed in our co-pending application PCT/IN05/00337 dated on 13/10/2005, the enriched demethylated curcuminoids from *Curcuma longa* extract is a potent 5-lipoxygenase enzyme inhibitor and good antioxidant.

5-Lipoxygenase enzyme is responsible for the inflammation and obese people more often tend to get inflammation, therefore the present enriched demethylated curcuminoids from *Curcuma longa* extract having 15-100% of total demethylated curcuminoids (formula I-IV), particularly 95% of total demethylated curcuminoids is useful for the treatment of obesity, inflammation, reduces total serum cholesterol level, phospholipids, triglycerides and free radical mediated diseases.

Accordingly, in one embodiment, the dietary and pharmaceutical compositions of the present invention contain at least 1% by weight of enriched demethylated curcuminoids and biologically acceptable carrier or diluent and one or more of known anti-obesic agents for the treatment of weight loss, inflammatory diseases and free radical mediated diseases.

In another preferred embodiment, the present invention provides synergistic dietary/pharmaceutical compositions comprise at least two of the compounds or extracts selected from enriched demethylated curcuminoids from *Curcuma longa*, *Moringa oleifera* plant extract, *Murraya koenigii* plant extract and optionally containing one or more of known anti-obesic agents for treating obesity, inflammation and free radical mediated disorders.

The optional anti-obesic agents may be selected from one or more of Eucalyptus plant extract, (−)-hydroxycitric acid and its salts from *Garcinia* species, *Piper betle* extract, standardized *Curcuma longa* extract, *Holoptelia integrifolia*, *Gymnema sylvestre* extract, carnitine, *Phaseolus vulgaris* extract, Bitter orange (*Citrus aurantium*) extract, Chitosan, Conjugated linoleic acid, Glucomannan (Konjac plant extract), Green coffee bean extract, *Caralluma* extract, Sea weed extract, *Hoodia gordonii* extract, *Commiphora mukul* gum resin extract, *Zingiber officinalis* extract, *Allium saliva* extract, *Cissus quandrangularis*, chromium compound like chromium picolinate, chromium nicotinate, chromium polynicotinate (niacin-bound chromium), chromium histidinate, Green tea extract, Medium chain triglycerides like caproic acid, caprylic acid, capric acid, myristic acid and lauric acid, 5-Hydroxy-L-tryptophan, Hydroxy methylbutyrate, Branched-chain amino acids, DHEA, 7-KetoDHEA, sibutramine and Orlistat.

In another preferred embodiment, the invention provides synergistic dietary/pharmaceutical compositions comprising enriched demethylated curcuminoids from *Curcuma longa*, *Moringa oleifera* plant extract and *Murraya koenigii* plant extract and optionally containing one or more of biologically acceptable carriers.

The present invention particularly provides dietary/pharmaceutical compositions comprising enriched demethylated curcuminoids in the range between 1-25% by wt., *Moringa oleifera* plant extract in the range between 30-70% by wt., and *Murraya koenigii* plant extract in the range between 15-45% by wt. and one or more biologically acceptable carriers.

In the preferred embodiment of the present invention, the compositions comprise enriched demethylated curcuminoids in 5% by wt., *Moringa oleifera* plant extract in 60% by wt., and *Murraya koenigii* plant extract in 35% by wt., exhibited synergistic adipogensis activity (see table 1) and is useful for preventing and/or reducing adipose tissue mass.

In another embodiment, the present invention provides dietary/pharmaceutical compositions comprising enriched demethylated curcuminoids from *Curcuma longa* and *Moringa oleifera* plant extract and biologically acceptable carriers or diluents and optionally containing one or more of known anti-obesic agents. Accordingly, the compositions comprise enriched demethylated curcuminoids in the range between 1-25% by wt. and *Moringa oleifera* plant extract in the range between 10-75% by wt., and one or more biologically acceptable carriers.

In yet another embodiment, the invention provides dietary/pharmaceutical compositions comprising enriched demethylated curcuminoids from *Curcuma longa* and *Murraya koenigii* plant extract and biologically acceptable carriers or diluents and optionally containing one or more of known anti-obesic agents. Accordingly, the compositions comprise enriched demethylated curcuminoids in the range between 1-25% by wt. and *Murraya koenigii* plant extract in the range between 10-75% by wt., and one or more biologically acceptable carriers.

In a further embodiment, the invention provides dietary/pharmaceutical compositions comprising *Moringa oleifera* plant extract and *Murraya koenigii* plant extract and biologically acceptable carriers or diluents and optionally containing one or more of known anti-obesic agents. Accordingly, the compositions comprise *Moringa oleifera* plant extract in the range between 5-75% by wt. and *Murraya koenigii* plant extract in the range between 5-50% by wt., and one or more biologically acceptable carriers. The dietary/pharmaceutical compositions comprising *Moringa oleifera* plant extract and *Murraya koenigii* plant extract may optionally further comprise *Curcuma longa* extract in the range of 1-25% by wt In another preferred embodiment, the invention provides dietary/pharmaceutical compositions comprise enriched demethylated curcuminoids in the range between 2.5-15% by wt., *Moringa oleifera* plant extract in the range between 20-40% by wt., *Murraya koenigii* plant extract in the range between 10-25% by wt., *Piper betle* extract in the range of 5-10% by wt. and calcium/potassium double salt of (−)-hydroxycitric acid 10-20% by wt.

The dietary/pharmaceutical compositions of the present invention comprise enriched demethylated curcuminoids in the range between 2.5-15% by wt., *Moringa oleifera* plant extract in the range between 40-70% by wt., and *Murraya koenigii* plant extract in the range between 25-45% by wt., also exhibits good 5-Lipoxygenase enzyme inhibitory activity (see table 2) and is useful for reducing or preventing inflammation.

The above inventive dietary/pharmaceutical compositions comprise enriched demethylated curcuminoids in the range between 2.5-15% by wt., *Moringa oleifera* plant extract in the range between 40-70% and *Murraya koenigii* plant extract in the range between 25-45% also shows good antioxidant activity by superoxide free radical scavenging method (see table 3) and may be useful for preventing free radical mediated disorders such as cancer, Alzheimer's, Parkinson's and various cardiovascular diseases.

In the embodiment of the present invention, wherein the enriched demethylated curcuminoids from *Curcuma longa* having 95% of total demethylated curcuminoids (formula I-IV) is used in this composition and the total demethylated curcuminoids mixture having 5-100% of total demethylated curcuminoids (formula I-IV) could also be used. An enriched natural *Curcuma longa* extract containing 25-95% total curcuminoids, comprising 1-5% demethylcurcuminoids (formulae I-IV) may also be used.

Various solvents extracts of *Moringa oleifera* plant have been screened as part of this invention for anti-adipogenic activity and found that a particular extract having chemical compounds of formula V to VIII exhibited good activity and hence it has been used in these compositions.

Consequently, the invention also relates to the *Moringa oleifera* plant extracts and its manufacturing process.

The *Moringa oleifera* plant extract, which exhibits good anti-adipogenic activity contains Kaempferol-3-O-glucoside of formula V, Quercitin-3-O-glucoside of formula VI, Niazinin A of formula VII, Niazinin B of formula VIII.

Formula V

Formula VI

Formula VII

Formula VIII

Chemical structures of the components in *Moringa oleifera* plant extract

The anti-adipogenic *Moringa oleifera* plant extract contains Kaempferol-3-O-glucoside of formula V in the range of 0.2-5% by wt., Quercitin-3-O-glucoside of formula VI in the range of 0.5-20% by wt., Niazinin A of formula VII in the range of 0.01-3% by wt., Niazinin B of formula VIII in the range of 0.001-3% by wt.

In the embodiment of the present invention, the chemical components of the *Moringa oleifera* plant extract are purified using column chromatography and their chemical structures are deduced by physical and spectroscopic data such as M.P., IR, $^1$H NMR & Mass spectrometry.

In the embodiment of the present invention, wherein the extract derived from *Moringa oleifera* plant contains Kaempferol-3-O-glucoside of formula V in the range of 0.2-5% by wt., Quercitin-3-O-glucoside of formula VI in the range of 0.5-20% by wt., Niazinin A of formula VII in the range of 0.01-3% by wt., Niazinin B of formula VIII in the range of 0.001-3% by wt. exhibited good adipogensis activity (see table 1) and is useful for the treatment of weight loss.

The invention also relates to a manufacturing process to produce the *Moringa oleifera* plant extract and the said extract contain at least two of the following compounds Kaempferol-3-O-glucoside of formula V, Quercitin-3-O-glucoside of formula VI, Niazinin A of formula VII, Niazinin B of formula VIII, useful for the treatment of hyperlipidemia.

In a further embodiment, the *Moringa oleifera* plant extract is obtained by extracting whole plant or leaves or stem or bark or fruit with suitable solvents. Particularly, leaves of *Moringa oleifera* plant is used for the extraction. The extraction process involved the following steps. (a) drying of *Moringa oleifera* plant leaves under shade, (b) powdering the dried leaves, (c) extracting the powder either with alcohol or hydro alcohol for 2 to 3 hrs at ambient temperature, (d) repeating the extracting process for 2 to 3 times, (e) filtering the combined extracts and distilling the solvent at reduced pressure, (f) passing extract through a resin column using a suitable solvent and (g) blending with additives to get the compositions.

The process for producing *Moringa oleifera* plant extract, wherein the said solvent for extraction is selected from water, methanol, ethanol, isopropanol, ethyl acetate, acetone or mixtures thereof, preferably ethanol.

The process for producing *Moringa oleifera* plant extract, wherein the resin is a synthetic adsorbent resin of type R 20 and the solvent for elution is hydroalcohol, preferably 70-80% methanol.

The dietary and pharmaceutical compositions derived from *Moringa oleifera* plant extract contain at least 0.01% by weight of total ingredients of formula V to formula VIII and biologically acceptable carrier or diluent for the reduction of adipose tissue mass.

The inventors have also screened various solvents extracts of *Murraya koenigii* plant for anti-adipogenic activity and found that these extracts exhibited good activity and hence used these extract in the present anti-adipogenic and proly-polysis compositions.

Thus, the invention also relates to a manufacturing process to produce anti-adipogenic *Murraya koenigii* plant extracts.

In the embodiment of the present invention, wherein the said *Murray koenigii* plant extract is obtained by extracting whole plant or leaves or stem or bark or fruit with suitable solvent. Particularly, leaves of *Murraya koenigii* plant used for the extraction. The extraction process involved the following steps. (a) drying of *Murray koenigii* plant leaves under shade, (b) powdering the dried leaves, (c) extracting the powder either with alcohol or hydro alcohol for 2 to 3 hrs at ambient temperature, (d) repeating the extraction process for 2 to 3 times and (e) filtering the combined extracts and distilling the solvent at reduced pressure.

In another aspect, the invention provides the plant extract of *Murraya koenigii* containing phyto constituents, Mahanine of formula IX, Mahanimbine of formula X, isomahanine of formula XI, and Ecuchrisitm-B of formula XII.

Formula IX

Formula X

Formula XI

Formula XII

*Murraya koenigii* extract comprise Mahanine of formula IX in the range of 0.1-10% by wt, Mahanimbine of formula X in the range of 0.01-5% by wt, isomahanine of formula XI in the range of 0.01-3% by wt and Ecuchrisitm-B of formula XII in the range of 0.01-2.5% by wt.

The 60% methanol extract of *Murraya koenigii* plant leaves, which is having anti-adipogenic activity, is used in these compositions (Table 1). The other solvents extracts of *Murraya koenigii* could also be used in these compositions.

In another embodiment of the present invention, the compositions comprising *Murraya koenigii* plant extract as an active ingredient and biologically acceptable carrier or diluents exhibited good adipogenesis activity (Table 1) and is useful for preventing and/or reducing adipose tissue mass.

The dietary and pharmaceutical compositions contain at least 1% by weight of *Murraya koenigii* plant extract and biologically acceptable carrier or diluent for preventing and/or reducing adipose tissue mass.

In the embodiment of the present invention, wherein a synergistic dietary/pharmaceutical composition comprises enriched demethylated curcuminoids from *Curcuma longa*, *Moringa oleifera* plant extract and *Murraya koenigii* plant extract and biologically acceptable carrier and the said carrier is selected from aqueous or non aqueous excipients, such as microcrystalline cellulose, sodium lauryl sulphate, polyvidone etc.

The invention further describes a method of treating human beings and animals to prevent and/or reduce adipose tissue mass or reduces body weight, total serum cholesterol level, phospholipids and triglycerides, wherein said method comprises administering a pharmaceutically effective amount of the present inventive compositions or enriched demethylated curcuminoids in a known manner.

The invention further provides a method of treating a subject from an inflammatory disease, wherein said inflammatory disease result from biomolecules secreted from activated degranulated mast cells, said inflammatory disease being selected from the group consisting of osteoarthritis, cancer, fibromyalgia, atherosclerosis, inflammatory bowel disease, interstitial cystitis, irritable bowel syndrome, migraines, angia, chronic prostatitis, eczema, atherogenesis, arthritis, multiple sclerosis, psoriasis, sun burn, and periodontal disease, comprising the step of administering to said subject an effective amount of these compositions.

A method of preventing a subject suffering from free radical mediated disease, wherein said free radical mediated disease result from the radicals generated in the body, said free radical mediated disease being selected from cancer, Alzheimer's, Parkinson's and cardiovascular disease, comprising the step of administering to said subject an effective amount of these inventive compositions.

Advantages of the Present Invention
1. Useful for preventing and/or reducing adipose tissue mass.
2. Useful for the treatment of hyperlipidemia.
3. Useful to lower serum cholesterol, phospholipids and triglycerides.
4. Useful to burn calories.
5. Useful for reducing inflammation.
6. Useful for preventing radical mediated diseases.

The following examples, which include preferred embodiments, will serve to illustrate the practice of this invention, it being understood that the particulars shown are by way of example and for purpose of illustrative discussion of preferred embodiments of the invention.

Example 1

The leaves of the plant *Moringa oleifera* were dried under shade and pulverized. The powder (1 Kg) was extracted with methanol (5 L) at room temperature for 2 h. The extract was removed by filtration and the extraction process repeated for 3 more times on the spent raw material. The combined methanol extract was fine filtered through a supercel bed and evaporated the solvent under reduced pressure to get the extract as a paste (205 g). The extract contains Formula V (0.33%), Formula VI (1.56%), Formula VII (0.32%) and Formula VIII (0.09%), when analyzed by HPLC.

The above residue (55 g) was dissolved in 30% aqueous methanol (1 L) and loaded to an R 20 resin column (550 mL, synthetic adsorbent) and the column washed with water (1 L). The column was then eluted with 80% aqueous methanol and the eluant was evaporated under reduce pressure to give the enriched fraction of *Moringa oleifera* extract (10 g).

The enriched fraction contains Formula V (1.14%), Formula VI (11.88%), Formula VII (0.35%) and Formula VIII (0.1%), when analyzed by HPLC.

The components present in the *Moringa oleifera* plant extract are separated through extensive silica gel column chromatography and characterized by their physical and spectral data.

Physical and spectroscopic data of Kaempferol-3-O-glucoside (formula V): Mp 174-176° C.; IR (KBr): 3397, 1664, 1609, 1287, 1183, 1061, 1013 cm$^{-1}$; $^1$H NMR (400 MHz, DMSO-d$_6$): δ 3.18-3.02 (3H, m, glucose protons), 3.56 (1H, dd, J=9.6, 2.6 Hz, glucose proton), 3.62 (1H, m, glucose proton), 3.82 (1H, d, J=9.0 Hz, glucose proton), 5.46 (1H, d, J=7.0 Hz, glucose anomeric proton), 6.20 (1H, d, J=3.3 Hz, H-6), 6.40 (1H, d, J=2.4 Hz, H-8), 6.88 (2H, J=8.4 Hz, H-3', 5'), 8.05 (2H, d, J=9.0 Hz, H-2',6'); LCMS: m/z 447 (M-H)$^-$.

Physical and spectroscopic data of Quercetin-3-O-glucoside (formula VI): Mp 224-226° C.; IR (KBr): 3368, 2926, 1664, 1609, 1198, 1060, 1030, 936, 800 cm$^{-1}$; $^1$H NMR (400 MHz, DMSO-d$_6$): δ 3.07 (1H, m, glucose proton), 3.20 (1H, m, glucose proton), 3.35 (1H, m, glucose proton), 3.59 (1H, m, glucose proton), 4.26 (2H, m, glucose proton), 5.46 (1H, d, J=7.0 Hz, glucose anomeric proton), 6.19 (1H, d, J=2.0 Hz, H-6), 6.39 (1H, d, J=2.0 Hz, H-8), 6.85 (1H, J=8.0 Hz, H-5'), 7.58 (1H, d, J=2.0 Hz, H-2'), 7.58 (1H, dd, J=8.0, 2.0 Hz, H-6'); LCMS: m/z 463 (M-H)$^-$.

Physical and spectroscopic data of Niazinin A (formula VII): IR (KBr); 3356, 1611, 1230, 1062, 772 cm$^{-1}$; $^1$H NMR (400 MHz, DMSO-d$_6$): δ 1.09 (3H, d, J=6.0 Hz, —CH$_3$), 3.26 (1H, dd, J=9.5, 6.0 Hz, H-4'), 3.44 (1H, d, J=6.3 Hz, H-5'), 3.62 (1H, dd, J=9.22, 6.0 Hz, H-3'), 3.81 (1H, dd, J=9.5, 5.9 Hz, H-2'), 3.85 (s, —OCH$_3$), 3.93 (s, —OCH$_3$), 4.25 (1H, d, J=6.3 Hz, H-7α), 4.56 (1H, d, J=6.1 Hz, H-7β), 5.32 (1H, d, J=1.8 Hz, H-1'), 6.98 (2H, d, J=8.4 Hz, H-2,6), 7.21 (2H, d, J=7.8 Hz, H-3,5), 9.56 (1H, t, J=6.1 Hz, —NH); LCMS: m/z 342 (M-H)$^-$.

Physical and spectroscopic data of Niazinin B (formula VIII): IR (KBr): 3400, 1600, 1040 cm$^{-1}$; $^1$H NMR (400 MHz, DMSO-d$_6$): δ 1.09 (3H, d, J=6.3 Hz, —CH$_3$), 3.26 (1H, dd, J=9.3, 5.70 Hz, H-4'), 3.40 (1H, dd, J=9.0, 6.3 Hz, H-5'), 3.61 (1H, dd, J=9.3, 6.1 Hz, H-3'), 3.80 (1H, dd, J=6.1, 4.4 Hz, H-2'), 3.86 (3H, s, —OCH$_3$), 4.24 (1H, d, J=6.0 Hz, H-7α), 4.31 (1H, t, J=6.1 Hz, —NH), 4.56 (1H, d, J=5.7 Hz, H-7β), 5.32 (1H, d, J=1.8 Hz, H-1'), 6.98 (2H, d, J=8.7 Hz, H-2,6), 7.21 (2H, d, J=7.8 Hz, H-3.5); LCMS: m/z 342 (M-H)$^-$.

Example 2

The leaves of the plant *Murraya koenigii* were dried under shade and pulverized to get a powder. The powder (1 Kg) was stirred with 60% methanol (5 L) at room temperature for 2 h. The extract was removed by filtration and the extraction process is repeated for 3 more times on the spent raw material. The combined extracts were fine filtered through a supercel bed and evaporated the solvent under reduced pressure to get the extract as a paste (220 g). The extract contains Formula IX (1.99%), Formula X (0.83%), Formula XI (0.59%) and Formula XII (0.32%), when analyzed by HPLC.

Example 3

Composition 1: A composition was prepared by mixing unit doses of the following components

| | |
|---|---|
| Enriched demethylated curcuminoids | 200 mg |
| Moringa oleifera leaf extract | 2.4 g |
| Murraya koenigii leaf extract | 1.4 g |

Example 4

Composition 2: A composition was prepared by mixing unit doses of the following components

| | |
|---|---|
| Enriched demethylated curcuminoids | 200 mg |
| Moringa oleifera leaf extract | 1.0 g |
| Murraya koenigii leaf extract | 800 mg |

Example 5

Composition 3: A composition was prepared by mixing unit doses of the following components

| | |
|---|---|
| Enriched demethylated curcuminoids | 200 mg |
| Moringa oleifera leaf extract | 1.2 g |
| Murraya koenigii leaf extract | 600 mg |

Example 6

Assessment of inhibition of lipid accumulation in differentiated adipocytes:

One hundred thousand 3T3-L1 Human pre-adipocyte cells in Dulbeccos Modified Eagles Medium (DMEM) containing 10% Fetal Bovine Serum (FBS) were taken into each well of a 24-well plate and incubated for 48 h at 37° C. and 5% $CO_2$. The differentiation of pre-adipocyte cells was initiated in a differentiation medium containing 10 µg/ml insulin, 1.0 µM dexamethasone, and 0.5 mM isobutylmethylxanthine (IBMX) for 48 h. After this the medium was replaced by DMEM containing 10 µg/ml insulin and incubated for 3 days. Then the differentiating cells were treated separately with 10 µg/ml of enriched demethylated curcuminoids or methanol extracts of Moringa oleifera leaf or Murraya koenigii leaf separately or their compositions and maintained in the medium for another 3-5 days. The cells incubated with 0.1% DMSO were considered as the vehicle control. After the incubation period, cells were washed with phosphate buffered saline (PBS) and fixed with 10% buffered formalin for 1 h at room temperature. One small aliquot of cell suspension was separated for cell counting in hemocytometer chamber. Fixed cells were stained with Oil Red O solution to measure the cellular neutral lipid accumulation. Briefly, cells were washed with PBS, fixed with 10% buffered formalin and stained with Oil Red O solution (0.5 g in 100 ml isopropanol) for 10 min. After removing the staining solution, the dye retained in the cells was eluted using isopropanol and OD was measured at 550 nm. The inhibition of fat accumulation in the treated cells was compared with the mock treated differentiated adipocytes. The treated cells and the control cells were also analyzed and compared for inhibition of lipid accumulation visually under microscope and recorded digitally in suitable image capture system. The % inhibition of lipid accumulation exhibited by enriched demethylated curcuminoids, methanol extracts of Moringa oleifera leaf and Murraya koenigii leaf or their compositions is summarized in table 1.

TABLE 1

Anti-obesity activity (adipogenesis activity)

| S. No. | Compound | Concentration (µg/mL) | % of inhibition* |
|---|---|---|---|
| 1 | Enriched demethylated curcuminoids | 10 | 29.50 |
| 2 | Moringa oleifera leaf extract | 10 | 25.70 |
| 3 | Murraya koenigii leaf extract | 10 | 24.86 |
| 4 | Composition 1 | 10 | 25.56 |
| 5 | Composition 2 | 10 | 40.50 |
| 6 | Composition 3 | 10 | 39.89 |

*The higher the % inhibition values, the higher the activity.

From the above adipogenesis inhibitory values (Table 1), it clearly shows the synergism of the compositions. For example, at 10 µg/mL concentration, the enriched demethylated curcuminoids, Moringa oleifera leaf extract and Murraya koenigii leaf extract exhibited 29.50%, 25.70% and 24.86% inhibition respectively, whereas, the compositions 2 & 3 exhibited 40.50% and 39.89% respectively. This inhibitory value of the compositions 2 and 3 is higher than the individual components of the compositions.

Example 7

Protective effect of composition-1 (A combination of unit doses of demethylated curcuminoids 95% and methanol extracts of Moringa oleifera leaf and Murraya koenigii leaf in the ratio of 1:12:7) against diet induced obesity in rats:

Selected healthy Sprague-Dawley rats were randomly assigned to control or various treatment groups (n=6). All the animals allocated for protective phase of the study were on dietary intervention by feeding high fat diet ad libitum and the animals allocated to treatment groups were simultaneously given oral administration of 250 mg/kg of composition-1 or 7 mg/kg sibutramine per day in 10 mL of 0.5% CMC, using gastric tube for the entire 8 week study duration. The test animals of the control group were simultaneously given 10 ml/kg of 0.5% CMC. Food and water consumption were recorded daily, body weights were recorded weekly and fasting blood samples were collected before initiation, after $4^{th}$ week and $8^{th}$ week (termination) of the study. The treatment groups supplemented with 250 mg/kg of composition-1 showed 21.5% reduction respectively in weight gain, against diet induced obesity, when compared with untreated control group (FIG. 1). The sibutramine supplemented treatment group showed 28.2% reduction in weight gain. The animals of the treatment group also showed significant reductions in serum triglycerides and lipid profile (anti-hyperlipidemic activity).

Example 8

Anti-obese activity of composition 1 in eiet induced obese rats:

Selected healthy Sprague-Dawley rats were randomly assigned to control or various treatment groups (n=6). All the animals allocated for the study were made obese through dietary intervention by feeding high fat diet ad libitum for 8 weeks. After 8 weeks, the treatment groups of animals were given oral administration of 250 mg/kg of composition-1 per day in 10 mL of 0.5% CMC, using gastric tube for 8 week study duration. The animals of control group were given 10 ml/kg of 0.5% CMC. Food and water consumption were recorded daily, body weights were recorded weekly and fasting blood samples were collected before initiation, after 4$^{th}$ week and 8$^{th}$ week (termination) of the study. The reduction in mean body weight gain of animals in treatment group supplemented with 250 mg/kg of composition-1 is 13.2%, compared to those in the untreated control group (FIG. 2). The treatment group of animals also showed significant reduction in serum triglycerides and lipid profile (antihyperlipidemic activity).

Example 9

Figure 3:
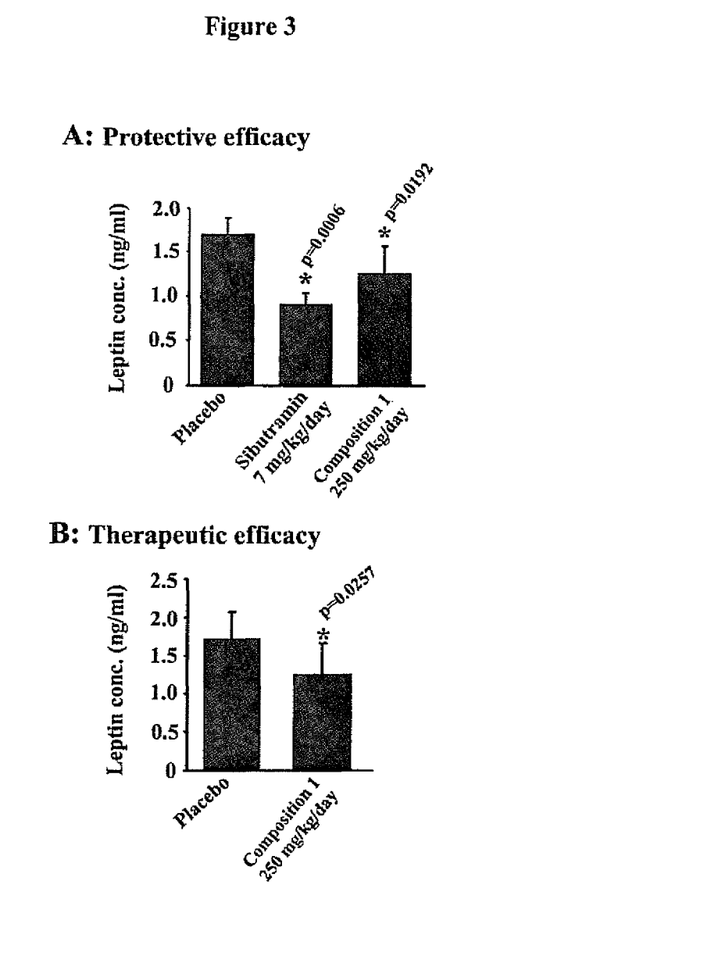
FIG. 3 presents bar diagrammatic representation of reduction of serum leptin concentrations (ng/ml) in protective (A) and therapeutic (B) efficacy evaluation of test compounds in diet induced obese rats. The numbers 1, 2 and 3 in FIG. 3A represent serum leptin levels in the placebo, sibutramine and composition-1 treated groups respectively. The numbers 1 and 2 in FIG. 3B represent serum leptin levels in the placebo and composition-1 treated groups respectively. Each bar represents mean±SD of data obtained from 6 animals. Serum leptin level was measured by Rat Leptin ELISA kit. The P values are obtained from t-test, compared with the placebo group.

Effect of composition 1 on serum leptin concentration in diet induced obese animals during the protective efficacy and treatment efficacy evaluation studies and comparison with leptin level of control group of animals:

Serum leptin concentration was quantitatively measured by a sandwich Elisa. The assay procedure was based on the instructions provided by the vendor (Linco Research, USA). The serum samples collected from treatment group of animals supplemented with composition 1 (example #s 7 and 8) and control group were selected and subjected to leptin analysis. Leptin present in the treatment group and control group rat serum samples was bound on the antiserum coated 96-well micro-titer plate. Biotinylated detection antibody was allowed to hind with the immobilized leptin and thereafter, horseradish peroxides enzyme was incubated to bind with the biotinylated conjugates. After washing away of the free enzyme the specifically bound enzyme activity was detected in presence of the substrate 3,3',5,5'-tetramethylbenzidene. The enzyme activity was measured spectrophotometrically at 450 nm. The concentration of leptin in the rat serum was measured by interpolation from a reference curve generated with the reference standards of known concentrations of rat leptin. The sensitivity of this assay is 0.04 ng/ml of leptin in rat serum. The mean serum leptin levels for different treatment groups supplemented with composition 1 (250 mg/kg dose, example # 7) for protection against diet induced obesity and control (placebo) group are summarized in FIG. 3A. The mean serum leptin levels for treatment group supplemented with composition 1 (250 mg/kg dose, example # 8) for treatment against diet induced obesity, and that of control group are summarized in FIG. 3B. All the treatment groups exhibited significant reduction in serum leptin levels compared to control group of animals.

Example 10

5-lipoxygenase inhibitory activity:

The new dietary/pharmaceutical supplement compositions are screened for their 5-lipoxygenase inhibitory potential using colorimetric method. The assay mixture contained 50 mM phosphate buffer (pH 6.3), 5-lipoxygenase, various concentrations of test composition (5 µg, 10 µg, 20 µg) in dimethylsulphoxide and linolenic acid in a total volume of 0.5 mL, after 5 min incubation of above reaction mixture 0.5 mL ferric xylenol orange reagent is added and OD is measured after two minutes at 585 nm using spectrophotometer. Controls are run along with test in a similar manner except using vehicle instead of test substance solution. Percent inhibition is calculated by comparing absorbance of the test solution with that of control.

The results are summarized in the following table

TABLE 2

5-Lipoxygenase inhibitory activity

| | | % of inhibition | |
|---|---|---|---|
| S. No. | Composition/compound | 5 µg | 10 µg |
| 1 | Composition 1 | 6.91 | 16.23 |
| 2 | Composition 2 | 20.24 | 41.37 |
| 3 | Composition 3 | 19.87 | 32.07 |
| 4 | NDGA | 50.2 | 77.35 |

The higher the % inhibition values, the higher the activity.
NDGA: Nordihydroguiaretic acid.

Example 11

Antioxidant activity of the compositions:

The dietary/pharmaceutical supplement compositions were screened for their antioxidant activity by superoxide free radical-scavenging method. The superoxide free radical-scavenging activity was determined by the NBT (nitro blue tetrazolium) method. The reaction mixture contained EDTA (6.6 mM), NaCN (3 µg), riboflavin (2 µM), NBT (50 µM), various concentrations of the test compositions in ethanol and a phosphate buffer (58 mM, pH 7.8) in a final volume of 3 ml. Optical density was measured at 560 mm The test tubes were uniformly illuminated with an incandescent lamp for 15 min, after which the optical density was measured again at 560 nm. The percentage inhibition and superoxide radical generation was measured by comparing the absorbance values of the control and those of the test compounds.

TABLE 3

Antioxidant activity

| S. No. | Composition/compound | Superoxide (NBT) IC$_{50}$ µg |
|---|---|---|
| 1 | Composition 1 | 51.83 |
| 2 | Composition 2 | 33.94 |
| 3 | Composition 3 | 36.31 |
| 4 | Vitamin C | 145 |
| 5 | BHT | 105 |

The lower the IC$_{50}$ values, the higher the antioxidant activity.
BHT: Butylated hydroxytoluene It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A synergistic anti-adipogenic and pro-lipolytic composition for the amelioration of adipogenesis and lipolysis mediated diseases, comprising:
   about 10% by weight of enriched demethylated curcuminoids obtained from *Curcuma longa*; and a combination of a *Moringa oleifera* leaf extract and a *Murraya koenigii* leaf extract;

said compositions optionally further containing at least one anti-obesic agent, at least one biologically acceptable carrier, or a mixture thereof;

wherein said composition contains said *Moringa oleifera* leaf extract in the range of 30-70% by wt., and said *Murraya koenigii* leaf extract in the range of 15-45% by wt.

2. The composition as claimed in claim 1, wherein the enriched demethylated curcuminoids comprise at least one compound selected from the group consisting of a compound of the formula I, a compound of the formula II, a compound of the formula III, a compound of the formula IV, and a mixture thereof:

said at least one compound being obtained by demethylation of *Curcuma longa* extract.

3. The composition as claimed in claim 1, wherein said *Moringa oleifera* leaf extract contains at least two of the following compounds: Kaempferol-3-O-glucoside of formula V, Quercitin-3-O-glucoside of formula VI, Niazinin A of formula VII, and Niazinin B of formula VIII:

Formula V

Formula VI

Formula VII

Formula VIII

4. The composition as claimed in claim 3, wherein said *Moringa oleifera* leaf extract comprises Kaempferol-3-O-glucoside of formula V in the range of 0.2-5% by wt., Quercitin-3-O-glucoside of formula VI in the range of 0.5-20% by wt., Niazinin A of formula VII in the range of 0.01-3% by wt., and Niazinin B of formula VIII in the range of 0.001-3% by wt.

5. The composition as claimed in claim 1, wherein said *Murraya koenigii* leaf extract is obtained by extracting a *Murraya koenigii* leaf with a solvent selected from the group consisting of water, methanol, ethanol, propanol, butanol, ethyl acetate, chloroform, dichloromethane, acetone and mixtures thereof.

6. The composition as claimed in claim 1, wherein the anti-obesic agents for optional addition are selected from the group consisting of *Holoptelia integrifolia* extract, Piper betle, standardized *Curcuma longa* extract, *Boerhaavia diffusa* extract, *Tribulus terrestris* extract, *Garcinia cambogia* extract, green tea extract, green coffee bean extract, Eucalyptus plant extract, *Gymnema sylvestre* extract, Banaba extract, carnitine, *Phaseolus vulgaris* extract, Bitter orange (*Citrus aurantium*) extract, chitosan, conjugated linoleic acid, Glucomannan (Konjac plant extract), green coffee bean extract, *Caralluma* extract, seaweed extract, *Hoodia Gordonii* extract, *Commiphora mukul* gum resin extract, *Zingiber officinalis* extract, *Allium sativum* extract, chromium picolinate, chromium nicotinate, chromium polynicotinate (niacin-bound chromium), chromium histidinate, caproic acid, caprylic acid, capric acid, myristic acid and lauric acid, 5-hydroxy-L-tryptophan, 4-hydroxyisoleucine, hydroxy methylbutyrate, branched-chain amino acids, double salts of (−)hydroxycitric acid from *Garcinia* species, DHEA, 7-KetoDHEA, sibutramine, orlistat and mixtures thereof.

7. The composition as claimed in claim 1, further comprising effective amounts of at least one pharmaceutically or nutritionally or dietetically acceptable antioxidant, adaptogen, anti-inflammatory agent, antidiabetic agent, *Curcuma longa* extract, *Piper nigrum* or *Piper longum* extract, trace metal, or mixture thereof to form a formulation.

8. The composition as claimed in claim 1, wherein the said compositions are in the form of a dietary formulation as a food for specified health uses.

9. The composition as claimed in claim 1, wherein said composition further comprise a pharmaceutically or nutraceutically or dietetically or veterinary acceptable additive, selected from the group consisting of a binder, a diluent, an antioxidant and a lubricant.

10. The composition as claimed in claim 1, wherein said enriched demethylated curcuminoids and said combination of said *Moringa oleifera* extract and said *Murraya koenigii* extract are present in amounts which are effective to reduce adipose tissue mass, body weight, total serum cholesterol level, phospholipids and triglycerides.

11. A therapeutic formulation, comprising a composition as claimed in claim 1, wherein said enriched demethylated curcuminoids and said combination of said *Moringa oleifera* leaf extract and said *Murraya koenigii* leaf extract are present in said therapeutic formulation in amounts which are effective for inhibiting 5-lipoxygenase.

12. The composition as claimed in claim 1, said compositions being in the form of pharmaceutical or dietary or veterinary or nutraceutical or cosmetic formulations.

13. A therapeutic formulation containing a composition as claimed in claim 1, said composition being present in an effective amount for reduction of adipose tissue mass, body weight, total serum cholesterol level, phospholipids, and triglycerides.

14. The composition as claimed in claim 2, wherein the enriched demethylated curcuminoids comprise from 90% to 95% by weight of the enriched demethylated curcuminoids of at least one compound selected from the group consisting of a compound of the formula I, a compound of the formula II, a compound of the formula III, a compound of the formula IV, and a mixture thereof.

15. The composition as claimed in claim 8, wherein the food for specified health uses is a chocolate bar, a nutritional bar, a cream, a jam a gel, a coffee, a tea, a milk-containing beverage, a lactic acid bacteria-containing beverage, a drop, a candy, a chewing gum, a chocolate, a gummy candy, a yoghurt, an ice cream, a pudding, a soft adzuki-bean jelly, a jelly, or a cookie.

16. The composition as claimed in claim 1, wherein said *Murraya koenigii* leaf extract contains at least two of the following compounds: Mahanine of formula IX, Mahanimbine of formula X, isomahanine of formula XI and Ecuchrisitm-B of formula XII:

Formula IX

Formula X

Formula XI

Formula XII

17. The composition as claimed in claim 16, wherein said *Murraya koenigii* leaf extract comprise Mahanine of formula IX in the range of 0.1-10% by wt, Mahanimbine of formula X in the range of 0.01-5% by wt, isomahanine of formula XI in the range of 0.01-3% by wt and Ecuchrisitm-B of formula XII in the range of 0.01-2.5% by wt.

18. The composition as claimed in claim 4, wherein the *Moringa oleifera* leaf extract is prepared by a process comprising the steps of:
 (i) drying a *Moringa oleifera* leaf in shade, followed by powdering said leaf to form a dry powder;
 (ii) extracting the dry powder with a suitable solvent and filtering; and
 (iii) distilling off the solvent at reduced pressure to obtain a residue.

19. The composition as claimed in claim 18, wherein the process for preparing the *Moringa oleifera* leaf extract further comprises:
 (iv) dissolving the said residue in 30% methanol to form a solution;
 (v) charging the said solution to a resin column followed by washing with water;
 (vi) eluting with 80% methanol to obtain a solution of active fraction; and
 (vii) evaporating the solvent from the solution of active fraction to obtain the active fraction.

20. An anti-adipogenic and prolipolytic composition for the amelioration of adipogenesis and lipolysis mediated diseases, consisting essentially of:
 a *Moringa oleifera* leaf extract and a *Murraya koenigii* leaf extract,
 wherein said *Moringa oleifera* leaf extract is in the range of 50-67% by wt., based on the combined weight of said *Murraya koenigii* leaf extract and said *Moringa oleifera* leaf extract; said *Moringa oleifera* leaf extract comprising at least two of Kaempferol-3-O-glucoside, Quercitin-3-O-glucoside, Niazinin A, and Niazinin B,
 said anti-adipogenic and pro-lipolytic composition optionally further comprising a biologically acceptable carrier;

wherein said anti-adipogenic and pro-lipolytic composition do not include enriched demethylated curcuminoids.

21. The composition as claimed in claim 20, wherein said compositions further comprise a pharmaceutically or nutraceutically or dietetically or veterinary acceptable additive, selected from binder, diluent, antioxidant and a lubricant.

22. A composition consisting essentially of:
a *Murraya koenigii* leaf extract, and
a *Moringa oleifera* leaf extract in the range of 50-67% by wt., based on the combined weight of said *Murraya koenigii* leaf extract and said *Moringa oleifera* leaf extract;
said *Moringa oleifera* leaf extract comprising at least two of Kaempferol-3-O-glucoside, Quercitin-3-O-glucoside, Niazinin A, and Niazinin B;
wherein said composition does not include enriched demethylated curcuminoids.

23. A composition for oral administration, comprising the composition of claim 22.

24. A method of weight control, comprising administering an effective amount of the composition as claimed in claim 1, said composition being formulated as a dairy product, an alcoholic beverage, a non-alcoholic beverage, or a snack bar.

25. A method for treating a subject to reduce adipose tissue mass, body weight, total serum cholesterol level, phospholipids or triglycerides comprising administering a biologically acceptable amount of the composition as claimed in claim 1.

26. The method of claim 25, wherein the subject is a mammal.

27. A process for the preparation of the composition according to claim 20, comprising the steps of:

(i) drying a *Moringa oleifera* leaves in shade, followed by powdering said plant part to form a dry powder;
(ii) extracting the dry powder with a suitable solvent and filtering;
(iii) distilling off the solvent at reduced pressure to obtain a residue;
(iv) optionally dissolving the said residue in 30% methanol to form a solution;
(v) optionally charging the said solution to a resin column followed by washing with water;
(vi) optionally eluting with a polar solvent to obtain a solution of active fraction; and
(vii) optionally evaporating the solvent from the solution of active fraction to obtain the active fraction; and
(viii) combining the residue of step (iii) or the active fraction of step (vii) with *Murraya koenigii* leaf extract in the range of 33-50% by wt.

28. The process as claimed in claim 27, wherein the said suitable solvent for extraction is selected from the group consisting of water, methanol, ethanol, isopropanol, ethyl acetate, acetone, and mixtures thereof.

29. The process as claimed in claim 27, wherein the said resin column comprises a resin selected from the group consisting of cationic exchange resin, anionic exchange resin, and synthetic adsorbent resins; and the solvent for elution is water or alcohol or mixtures thereof.

30. A method for treating a subject to reduce adipose tissue mass, body weight, total serum cholesterol level, phospholipids and triglycerides comprising administering a biologically acceptable amount of a composition as claimed in claim 20.

\* \* \* \* \*